United States Patent [19]

Creger et al.

[11] Patent Number: 4,882,357

[45] Date of Patent: Nov. 21, 1989

[54] NOVEL N-(SUBSTITUTED-PHENYL)-5-(SUBSTITUTED-2,5-DIMETHYLPHENOXY)-2,2-DIMETHYLPENTANAMIDES

[75] Inventors: Paul L. Creger; Milton L. Hoefle, both of Ann Arbor; Ann Holmes, Dexter, all of Mich.

[73] Assignee: Warner-Lambert Company, Morris Plains, N.J.

[21] Appl. No.: 219,964

[22] Filed: Jul. 15, 1988

[51] Int. Cl.$^4$ .................. A61K 31/165; C07C 103/22
[52] U.S. Cl. .................................... 514/622; 514/546; 514/539; 514/533; 564/175; 560/138; 560/45; 560/21
[58] Field of Search .................. 564/175; 560/138, 45, 560/21; 514/622, 533, 539, 546, 548

[56] References Cited

U.S. PATENT DOCUMENTS 4,413,011  11/1983  Sircar et al. ..................... 424/309
4,465,507   8/1984  Konno et al. ...................... 71/98
4,554,282  11/1985  Sircar et al. ..................... 514/357

*Primary Examiner*—Nicky Chan
*Attorney, Agent, or Firm*—Francis J. Tinney

[57] ABSTRACT

Novel N-(substituted-phenyl)-5-(substituted-2,5-dimethylphenoxy)-2,2-dimethylphentanamides which are useful in preventing the intestinal absorption of cholesterol and also increasing high-density lipoprotein (HDL) cholesterol, as well as novel pharmaceutical compositions and methods of use, as well as processes for their manufacture are herein described.

12 Claims, No Drawings

NOVEL N-(SUBSTITUTED-PHENYL)-5-(SUBSTITUTED-2,5-DIMETHYLPHENOXY)-2,2-DIMETHYLPENTANAMIDES

BACKGROUND OF THE INVENTION

The present invention relates to novel substituted amides useful as pharmaceutical agents, to methods for their production, to pharmaceutical compositions which include these compounds and a pharmaceutically acceptable carrier, and to a pharmaceutical method of treatment. More particularly, the novel compounds of the present invention lower low density lipoprotein choesterol (LDL) and elevate high density lipoprotein cholesterol (HDL). Both of these effects afford protection from coronary heart disease.

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. Two recent clinical trials have shown a causal relationship between serum levels of LDL- and HDL-cholesterol and coronary heart disease.

In 1984, the Lipid Research Clinics-Coronary Prevention Trial (LRC-CPPT) demonstrated for the first time that lowering LDL cholesterol would reduce coronary heart disease. Very recently the results of a five-year, 4,081-patient clinical trial published in the *New England Journal of Medicine*, 317, pp 1237–1245 (1987) demonstrated that the lipid regulating drug, gemfibrozil, reduced the rate of heart attack and sudden cardiac death by 34 percent in patients with elevated cholesterol levels. Gemfibrozil both lowers LDL and elevates HDL; but if the results from the LRC-CPPT study are utilized to estimate the expected reduction in incidence of heart attack and heart disease due to lowering of LDL, it amounts to approximately one-half of the effect actually observed. Thus, there appears to be little doubt as to the benefit of elevating HDL.

The compounds of this invention combine two mechanisms of action to achieve their improved activity in lowering LDL and elevating HDL. Not only do they show the same effects as gemfibrozil but, in addition, they inhibit the enzyme acyl-CoA:cholesterol acyltransferase (ACAT).

Dietary cholesterol is absorbed from the intestinal lumen as free cholesterol which must be esterified with fatty acids. This reaction is catalyzed by ACAT. The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering LDL cholesterol levels and ultimately preventing the further development of atherosclerosis.

Prior work on amides of gemfibrozil (US 4,413,011 to Sircar, I and Holmes, A, issued November 1, 1983) identified those compounds that retained the original lipid modulating activity of the parent drug which is demonstrated by the elevation of HDL in rats. The present compounds differ in that they have been chosen for their superior inhibition of ACAT, and thus they possess two different mechanisms of action that complement each other. Thus, gemfibrozil speeds up the metabolism of LDL in the liver, and the excess cholesterol is released into the intestines via the bile. Normally a portion of this cholesterol is reabsorbed and ultimately recirculated in the form of new LDL. However, this is prevented in the presence of an ACAT inhibitor.

SUMMARY OF THE INVENTION

Accordingly, a first aspect of the present invention is a compound of Formula I

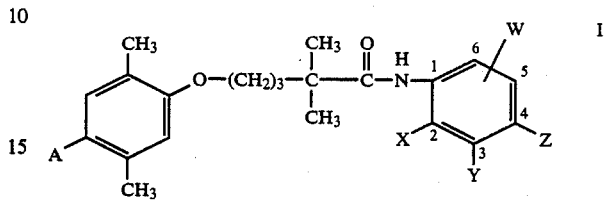

or a pharmaceutically acceptable acid addition salt thereof, wherein A is hydrogen, hydroxy, alkoxy of from one to six carbon atoms or

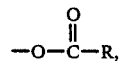

in which R is an alkyl group of from one to six carbon atoms; X and Y are each independently hydrogen, fluorine, nitro, —$NH_2$, —NHR, in which R is as defined above, —NRR, in which R is as defined above, alkyl of from one to six carbon atoms, alkoxy of from one to six carbon atoms which may be substituted at the terminal carbon atom by —$CO_2R$, in which R is as defined above; Z and W are each independently hydrogen, fluorine, alkyl of from one to six carbon atoms or alkoxy of from one to six carbon atoms, which may be substituted at the terminal carbon atom by —$CO_2R$, in which R is as defined above, and at least one of X, Y, Z or W is not hydrogen; or wherein one of X, Y, Z or W together with its vicinal member forms a methylenedioxy group.

Additionally, the present invention is directed to a pharmaceutical composition useful for inhibiting intestinal absorption of cholesterol and also for increasing high-density lipoprotein (HDL) cholesterol in mammals comprising an effective amount of a compound of Formula I as defined above with a pharmaceutically acceptable carrier.

Also, the present invention is directed to a novel method of inhibiting intestinal absorption of cholesterol and also increasing high-density lipoprotein (HDL) cholesterol in mammals comprising administering an effective amount of a compound of Formula I as defined above.

Finally the present invention is directed to methods for production of a compound of Formula I as defined above.

DETAILED DESCRIPTION OF THE INVENTION

In the compounds of Formula I, the term "alkyl" means a straight or branched hydrocarbon group havin9 from one to eight carbon atoms and includes, for example, methyl, ethyl, n-propyl, isopropyl, n-butyl, isobutyl, tertiary-butyl, n-pentyl, n-hexyl, n-heptyl, n-octyl, and the like.

"Alkoxy" is 0-alkyl in which alkyl is as defined above.

"Halogen" is iodine, bromine, chlorine, and fluorine.

A preferred group of compounds are those of Formula II

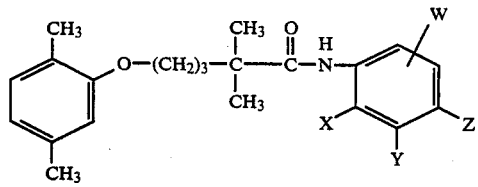

wherein X, Y, Z, and W are as defined above.

A most preferred group of compounds are those of Formula II wherein X is hydrogen, fluorine, alkyl of from one to six carbon atoms, or alkoxy of from one to six carbon atoms which may be substituted at the terminal carbon atom by —CO$_2$R in which R is as defined above; Y is hydrogen, nitro, —NH$_2$, —NHR, in which R is as defined above, -NRR, in which R is as defined above, alkyl of from one to six carbon atoms, or alkoxy of from one to six carbon atoms which may be substituted at the terminal carbon atom by —CO$_2$R, in which R is as defined above; Z is hydrogen, fluorine, alkyl of from one to six carbon atoms, alkoxy of from one to six carbon atoms which may be substituted at the terminal carbon atom by —CO$_2$R, in which R is as defined above, or Y and Z taken together form a methylenedioxy group; and W is hydrogen, fluorine, alkyl of from one to six carbon atoms, alkoxy of from one to six carbon atoms which may be substituted at the terminal carbon atom by —CO$_2$R, in which R is as defined above. Particularly valuable are: 5-(2,5-Dimethylphenoxy)-N-(2-methoxyphenyl)-2,2-dimethylpentanamide;

5-(2,5-Dimethylphenoxy)-N-(2-methoxy-4-methylphenyl)-2,2-dimethylpentamide;

5-(2,5-Dimethylphenoxy)-N-(2,4-dimethylphenyl)-2,2-dimethylpentanamide;

N-(3,4-Dimethoxyphenyl)-5-(2,5-dimethylphenoxy)-2,2-dimethylpentanamide;

5-(2,5-Dimethylphenoxy)-N-(2-ethoxyphenyl)-2,2-dimethylpentanamide;

5-(2,5-Dimethylphenoxy)-2,2-dimethyl-N-[2-(1-methylethoxy)phenyl]-pentanamide;

5-(2,5-Dimethylphenoxy)-N-[2-(hexyloxy)phenyl]2,2-dimethylpentanamide;

N-(2,4-Difluorophenyl)-5-(2,5-dimethylphenoxy)-2,2-dimethylpentanamide;

5-(2,5-Dimethylphenoxy)-2,2-dimethyl-N-(2,4,6-trifluorophenyl)pentanamide;

5-(2,5-Dimethylphenoxy)-2,2-dimethyl-N-(3-nitrophenyl)pentanamide;

5-(2,5-Dimethylphenoxy)-2,2-dimethyl-N-[4-methyl-2-(1-methylethoxy)phenyl]pentanamide;

N-1,3-Benzodioxol-5-yl-5-(2,5-dimethylphenoxy)2,2-dimethylpentanamide;

5-[3-[[5-(2,5-Dimethylphenoxy)-2,2-dimethyl-1oxopentyl]amino]phenoxy]-2,2-dimethylpentanoic acid, methyl ester;

5-[2-[[5-(2,5-Dimethylphenoxy)-2,2-dimethyl-1-oxopenyl]amino]henoxy-2,2-dimethylpentanoic acid, methyl ester;

N-(3-Aminophenyl)-5-(2,5-dimethylphenoxy)-2,2dimethylpentanamide;

5-[4-[[5-(2,5-dimethylphenoxy)-2,2-dimethyl-1oxopentyl]amino]phenoxy]-2,2-dimethylpentanoic acid, methyl ester; or a pharmaceutically acceptable acid addition salt thereof.

The process of preparing compounds of the present invention is described generally as follows:

A compound having the Formula I

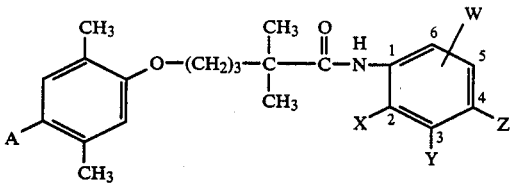

or a pharmaceutically acceptable acid addition salt thereof, wherein A is hydrogen, hydroxy, alkoxy of from one to six carbon atoms or

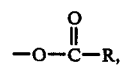

in which R is n alkyl group of from one to six carbon atoms; X and Y are each independently hydrogen, fluorine, nitro, —NH$_2$, NHR, in which R is as defined above, —NRR, in which R is as defined above, alkyl of from one to six carbon atoms, alkoxy from one to six carbon atoms which may be substituted at the terminal carbon atom by —CO$_2$R, in which R is as defined above; Z and W are each independently hydrogen, fluorine, alkyl of from one to six carbon atoms or alkoxy of from one to six carbon atoms, which may be substituted at the terminal carbon atom by —CO$_2$R, in which R is as defined above, and at least one of X, Y, Z or W is not hydrogen; or wherein one of X, Y, Z or W taken together with its vicinal member forms a methylenedioxy group; is prepared by coupling a compound of Formula III

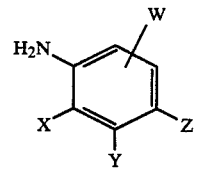

wherein X, Y, Z, and W are as described above with a compound of Formula IV

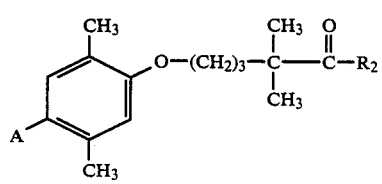

wherein R$_2$ is a leaving group and A is as described above.

Preferred coupling methods involve contacting a compound of Formula III with acylhalides of the Formula V

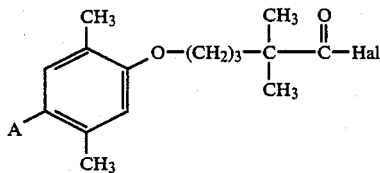

V wherein Hal is halogen, preferably chlorine or bromine and A is as described above. The reaction is carried out in nonaqueous solvent such as acetonitrile, tetrahydrofuran or methylene chloride, preferably methylene chloride, with an added organic base such as triethylamine or pyridine, preferably triethylamine, if needed at temperatures between −10° C. and the reflux temperature of the solvent, preferably at 0° C.

Compounds of Formula III are either known or capable of being prepared by methods known in the art.

Compounds of Formula IV are obtained by appropriately activating a compound of Formula VI

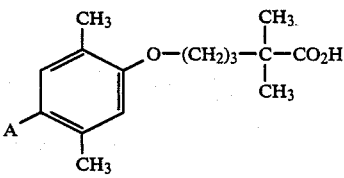

VI wherein A is as described above with a carboxyl activating group such as described in E. Schroeder and K. Lubke, "The Peptides," Vol. 1, Chapt. III, Academic Press, 1966.

Compounds of Formula VI are either known or capable of being prepared by methods known in the art.

A compound of Formula I also may be prepared by contacting a compound of Formula VII

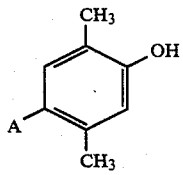

VII wherein A is as described above with a compound of Formula VIII

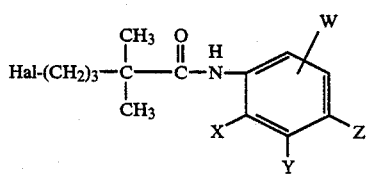

VIII wherein Hal, X, Y, Z, and W are as defined above. The reaction is carried out in the presence of a base such as, for example, sodium hydroxide, potassium carbonate, and the like in nonaqueous solvent such as, for example, tetrahydrofuran at temperatures between 0° C. and the reflux temperature of the solvent, preferably at the reflux temperature of the solvent.

Compounds of Formula VII are either known or capable of being prepared by methods known in the art.

Compounds of Formula VIII are obtained by contacting a compound of Formula IX

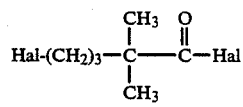

IX wherein Hal is as described above with a compound of Formula III.

The reaction is carried out in nonaqeous solvent such as acetonitrile, tetrahydrofuran or methylene chloride, preferably methylene chloride, with an added organic base such as triethylamine or pyridine, preferably triethylamine, if needed at temperatures between −10° C. and the reflux temperature of the solvent, preferably at 0° C.

Compounds of Formula IX are either known or capable of being prepared by methods known in the art.

The products of the reactions described herein are isolated by conventional means such as chromatography, recrystallization, distillation, and the like. Generally, the starting materials are known, commercially available, or synthesized by known methods.

The compounds of the present invention were tested for their ability to inhibit the esterification of cholesterol by the enzyme acyl-CoA:cholesterol acyltransferase (ACAT). The data in the table below is expressed as $IC_{50}$ values, i.e., the concentration of test compound required to inhibit cholesteryl oleate formation to 50% of control. The data in the table shows the ability of representative compounds of the present invention to potently inhibit ACAT.

The in vitro test employed is more fully described in Field, F. J. and Salome, R. G., Biochemica et Biophysica Acta, 712, pp 557–570 (1982). The assay evaluates the ability of a test compound to inhibit the esterification of cholesterol using endogenous cholesterol of a rabbit intestinal microsomal fraction and exogenous $^{14}C$-oleoyl-CoA as reactants.

Additionally, the elevation of HDL is reported in the table as a ratio of the elevation of HDL effected by a dose of 50 mg/kg of the test drug divided by the elevation of HDL effected by a 50 mg/kg dose of gemfibrozil which is used as a control in each experiment.

$$\text{HDL elevation} = \frac{\Delta \text{ HDL test drug}}{\Delta \text{ HDL gemfibrozil}}$$

Thus, a figure of 1 means that the test drug was as effective as gemfibrozil in elevating HDL. Values greater than 1 suggest that the test drug is more effective than gemfibrozil. The test procedure is described in U.S. Pat. No. 4,413,011.

TABLE

Biological Activity of Compounds of Formula I

| Example Number | Compound | $IC_{50}$ (μmoles) | $\frac{\Delta \text{HDL Test Drug}}{\Delta \text{HDL Gemfibrozil}}$ |
|---|---|---|---|
| 1a | 5-(2,5-Dimethylphenoxy)-N—(2-methoxy-4-methylphenyl)-2,2-dimethylpentanamide | 6 | 0.80 |
| 1b | 5-(2,5-Dimethylphenoxy)-N—(2,4-dimethylphenyl)- | 8 | 1.29 |

TABLE-continued
Biological Activity of Compounds of Formula I

| Example Number | Compound | IC$_{50}$ (μmoles) | $\frac{\Delta \text{HDL Test Drug}}{\Delta \text{HDL Gemfibrozil}}$ |
|---|---|---|---|
| 1d | 5-(2,5-Dimethylphenoxy)-N—(2-ethoxyphenyl)-2,2-dimethylpentanamide | 5 | 1.08 |
| 1c | N—(3,4-Dimethoxyphenyl)-5-(2,5-dimethylphenoxy)-2,2-dimethylpentanamide | 3 | 1.10 |
| 1j | 5-(2,5-Dimethylphenoxy)-2,2-dimethyl-N[4-methyl-2-(1-methylethoxy)phenyl]-pentanamide | 8 | 0.84 |
| 1g | N—(2,4-Difluorophenyl)-5-(2,5-dimethylphenoxy)-2,2-dimethylpentanamide | 7 | 0.36 |
| 1h | 5-(2,5-Dimethylphenoxy)-2,2-dimethyl-N—(2,4,6-trifluorophenyl)-pentanamide | 0.8 | 0.74 |
| 1k | N—1,3-Benzodioxol-5-yl-5-(2,5-dimethylphenoxy)-2,2-dimethylpentanamide | 6 | 1.13 |
| 1m | 5-[3-[[5-(2,5-Dimethylphenoxy)-2,2-dimethyl-1-oxopentyl]amino]phenoxy]-2,2-dimethylpentanoic acid, methyl ester | 21 | 1.0 |
| 1l | 5-[2-[[5-(2,5-Dimethylphenoxy)-2,2-dimethyl-1-oxopentyl]amino]phenoxy-2,2-dimethylpentanoic acid, methyl ester | 8 | 0.4 |
| 1 | 5-(2,5-Dimethylphenoxy)-N—(2-methoxyphenyl)-2,2-dimethylpentanamide | 14 | 0.31 |
| 1f | 5-(2,5-Dimethylphenoxy)-N—[2-(hexyloxy)phenyl]-2,2-dimethylpentanamide | 10 | 0.42 |
| Example 5 (U.S. Pat. No. 4,413,011) | 3-[4-[[5-(2,5-Dimethylphenoxy)-2,2-dimethyl-1-oxopentyl]amino]phenyl]-2-propenoic acid, ethyl ester | 45 | 0.56 |

Therefore, the compounds of the present invention are useful in pharmaceutical formulations for preventing absorption of dietary cholesterol or the reabsorption of cholesterol which has been released into the intestines through endogenous regulatory mechanisms and also for increasing HDL cholesterol levels.

The present invention also includes a method for treating hypercholesterolemia comprising administering to mammals, including humans, the corresponding pharmaceutical composition. The composition contains a compound of Formula I as defined before in an appropriate unit dosage form.

For preparing pharmaceutical compositions from the compounds of the present invention, pharmaceutically acceptable carriers can be either solid or liquid. Solid form preparations include powders, tablets, pills, capsules, and dispersible granules. A solid carrier can be one or more substances which may also act as diluents, flavoring agents, solubilizers, lubricants, suspending agents, binders, preservatives, tablet disintegrating agents or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water propylene glycol solutions.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet or lozenge itself or it can be the appropriate number of any of these in packaged form.

The quantity of active component in a unit dose preparation may be varied or adjusted from 50 mg to 500 mg, preferably 100 mg to 300 mg according to the particular application and the potency of the active component. The composition can, if desired, also contain other compatible therapeutic agents.

The dosage range for a 70-kg mammal is from 1 mg/kg to 100 mg/kg of body weight per day or preferably 3 mg/kg to 15 mg/kg of body weight per day when the compounds of the present invention are used therapeutically to inhibit the intestinal absorption of cholesterol and also increase HDL cholesterol levels. However, dosages may be varied depending upon the compound used, the severity of the condition being treated, and the requirements of the patient. Determination of the appropriate dosage for a particular situation is within the skill of the art.

The invention is further illustrated but not limited by the following examples.

EXAMPLE 1

5-(2,5-Dimethylphenoxy)-N-(2-methoxyphenyl)-2,2dimethylpentanamide

To a solution of 3.7 g (0.03 mol) of 2-methoxybenzenamine and 3.03 g (0.03 mol) of triethylamine in 100 ml of tetrahydrofuran is added dropwise with stirring 7.7 g (0.03 mol) of 5-(2,5-dimethylphenoxy)-2,2-dimethylpentamoyl chloride (US 4,285,951). The mixture is stirred at room temperature overnight, filtered, and the filtrate concentrated in vacuo. Water is added to the residue and the solid filtered to afford 7.9 g of 5-(2,5-dimethylphenoxy)-N-(2-methoxyphenyl)-2,2-dimethylpentanamide as a white solid after recrystallization from pentane mp 47°–48° C.

EXAMPLE 1a 5-(2,5-Dimethylphenoxy)-N-(2-methoxy-4-methylphenyl)-2,2-dimethylpentanamide In a process analogous to Example 1 by substituting 2-methoxy-4-methylbenzenamine (*Journal of Medicinal Chemistry* Vol 22 pp 63–69 (1979), for 2-methoxybenzeneamine one obtains 5-(2,5-dimethylphenoxy)-N-(2-methoxy-4-methylphenyl)-2,2-dimethylpentanamide; bp 190-195° C. (0.50 mm).

EXAMPLE 1b 5-(2,5-Dimethylphenoxy)-N-(2,4-dimethylphenyl)-2,2-dimethylpentanamide In a process analogous to Example 1 by substituting 2,4-dimethylbenzenamine for 2-methoxybenzenamine one obtains 5-(2,5-dimethylphenoxy)-N(2,4-dimethylphenyl)-2,2-dimethylpentanamide; mp 80°–82° C.

EXAMPLE 1c

N-(3,4-Dimethoxyphenyl)-5-(2,5-dimethylphenoxy)-2,2-dimethylpentanamide

In a process analogous to Example 1 by substituting 3,4-dimethoxybenzenamine for 2-methoxybenzenamine one obtains N-(3,4-dimethoxyphenyl)-5(2,5-dimethylphenoxy)-2,2-dimethypentanamide; mp 110°–111° C.

EXAMPLE 1d 5-(2,5Dimethylphenoxy)-N-(2-ethoxyphenyl)-2,2dimethylpentanamide

In a process analogous to Example 1 by substituting 2-ethoxybenzenamine for 2-methoxybenzenamine one obtains 5-(2,5-dimethylphenoxy)-N-(2-ethoxyphenyl)-2,2-dimethylpentanamide; mp 59°–60° C.

EXAMPLE 1e 5-(2,5-Dimethylphenoxy)-2,2-dimethyl-N[2-(1-methylethoxy)phenyl]pentanamide In a process analogous to Example 1 by substituting 2-(1-methylethoxy)benzenamine (Example A) for 2-methoxybenzenamine one obtains 5-(2,5-dimethylphenoxy)-2,2-dimethyl-N[2-(1-methylethoxy)phenyl]pentanamide as a viscous liquid.

EXAMPLE 1f 5-(2,5-Dimethylphenoxy)-N2-(hexyloxy)phenyl]-2,2- 0 -dimethylpentanamide In a process analogous to Example 1 by substituting 2-(hexyloxy)benzenamine (Example B) for 2-methoxybenzenamine one obtains 5-(2,5-dimethylphenoxy)-N[2-(hexyloxy)phenyl]-2,2-dimethylpentanamide as a viscous liquid.

EXAMPLE 1g

N-(2,4-Difluorophenyl)-5-(2,5-dimethylphenoxy)-2,2dimethylpentanamide

In a process analogous to Example 1 by substituting 2,4-difluorobenzenamine for 2-methoxybenzenamine one obtains N-(2,4-difluorophenyl)-5(2,5-dimethylphenoxy)-2,2-dimethylpentanamide; mp 79°–80° C.

EXAMPLE 1h 5-(2,5-Dimethylphenoxy)-2,2-dimethyl-N-(2,4,6trifluorophenyl)pentanamide In a process analogous to Example 1 by substituting 2,4,6-trifluorobenzenamine for 2-methoxybenzenamine one obtains 5-(2,5-dimethylphenoxy)-2,2-dimethyl-N-(2,4,6-trifluorophenyl)pentanamide; mp 82°–83° C.

EXAMPLE 1i 5-(2,5-Dimethylphenoxy)-2,2-dimethyl-N-(3-nitrophenyl)pentanamide In a process analogous to Example 1 by substituting 3-nitrobenzenamine for 2-methoxybenzenamine one obtains 5-(2,5-dimethylphenoxy)-2,2-dimethyl-N-(3-nitrophenyl)pentanamide; mp 93°–94° C.

EXAMPLE 1j 5-(2,5-Dimethylphenoxy)-2,2-dimethyl-N-[4-methyl-2-(1-methylethoxy)phenyl]pentanamide In a process analogous to Example 1 by substituting 4-methyl-2-(1-methylethoxy)benzenamine (Example C) for 2-methoxybenzenamine one obtains 5-(2,5-dimethylphenoxy)-2,2-dimethyl-N-[4-methyl-2(2-(1-methylethoxy)phenyl]pentanamide as a viscous liquid; bp 193°–197° C (0.50 mm).

EXAMPLE 1k

N-1,3-Benzodioxol-5-yl-5-(2,5-dimethylphenoxy)-2,2dimethylpentanamide

In a process analogous to Example 1 by substituting 1,3-benzodioxol-5-amine for 2-methoxybenzenamine one obtains N-1,3-benzodioxol-5-yl-5(2,5- dimethylphenoxy)-2,2-dimethylpentanamide; mp 89°–90° C.

EXAMPLE 11

5-(2-[[5-(2,5-Dimethylphenoxy)-2,2-dimethyl-1oxopentyl]amino]phenoxy]-2,2-dimethylpentanoic acid, methyl ester In a process analogous to Example 1 by substituting 5-(2-aminophenoxy)-2,2-dimethylpentanoic acid, methyl ester (Example D) for 2-methoxybenzenamine one obtains 5-[2[[5-(2,5-dimethylphenoxy)2,2-dimethyl- 1-oxopentyl]amino]phenoxy]-2,2-dimethylpentanoic acid, methyl ester as an oil; IR 1732, 1685 cm$^{-1}$.

EXAMPLE 1m

5-[3-[[5-(2,5-Dimethylphenoxy)-2,2-dimethyl-1-oxopentyl]amino]phenoxy]-2,2-dimethylpentanoic acid, methyl ester In a process analogous to Example 1 by substituting 5-(3-aminophenoxy)-2,2-dimethylpentanoic acid, methyl ester (Example E) for 2-methoxybenzenamine one obtains 5-[3-[[5-(2,5-dimethylphenoxy)-2,2-dimethyl-1-oxopentyl]amino]phenoxy]-2,2-dimethylpentanoic acid, methyl ester; IR 1732, 1661 cm$^{-1}$.

EXAMPLE 1n

5-[4-[[5-(2,5-Dimethylphenoxy)-2,2-dimethyl-1-oxopentyl]amino]-2,5-dimethylphenoxy]-2,2-dimethylpentanoic acid, methyl ester In a process analogous to Example 1 by substituting 5-[4-amino-2,5-dimethylphenoxy)-2,2-dimethylpentanoic acid, methyl ester (Example F) for 2-methoxybenzenamine one obtains 5-[4-[[5-(2,5-dimethylphenoxy)-2,2-dimethyl-1-oxopentyl]amino]-2,5-dimethylphenoxy]-2,2-dimethylpentanoic acid, methyl ester; mp 60°-62° C.

Example 2

5-4-[[5-(2,5-Dimethylphenoxy)-2,2-dimethyl-1oxopentyl]amino]phenoxy]-2,2-dimethylpentanoic acid, methyl ester In a process analogous to Example 1 by substituting 4-aminophenol for 2-methoxybenzenamine one obtains 5-(2,5-dimethylphenoxy)-N-(4-hydroxyphenyl)-2,2-dimethylpentanamide as an oil.

Sodium hydride, 50% dispersion in mineral oil, 2.2 g, is added to 15.3 g of 5-(2,5-dimethylphenoxy)-N-(4-hydroxyphenyl)-2,2-dimethylpentanamide in 200 ml of N,N-dimethylformamide (DMF). Then 10 g of methyl 5-bromo-2,2-dimethylpentanoate (*Journal of Medicinal Chemistry, Vol.* 26, pp 1020–1027 (1983)) is added to the previous mixture. The mixture is stirred overnight and then stirred three hours on a steam bath, the DMF is removed on a rotary evaporator and water is added to the residue. The product is taken up in diethyl ether, extracted with base, washed with water and concentrated on a steam bath. Isopropyl ether is added to afford 10.4 g of 5-[4-[[5-(2,5-dimethylphenoxy)-2,2-dimethyl-1-oxopentyl]amino]-phenoxy]-2,2-dimethylpentanoic acid, methyl ester after recrystallization from isopropyl ether (2X); mp 62°-63° C.

EXAMPLE 3

N-(3-Aminophenyl)-5-(2,5-dimethylphenoxy)-2,2-dimethylpentanamide 5-(2,5-Dimethylphenoxy)-2,2-dimethyl-N-(3-nitrophenyl)pentanamide (Example 1i), 22.39 g (0.0604 mol), is dissolved in 400 ml of methanol, 1.5 g of Raney nickel is added and the mixture is exposed to hydrogen gas until the required amount of hydrogen is absorbed. The methanol solution is filtered and concentrated in vacuo and the residue solidifes to afford 19.8 g of N-(3-aminophenyl)-5-(2,5-dimethylphenoxy)-2,2-dimethylpentanamide after recrystallization from isopropyl ether; mp 93°-94° C.

PREPARATIVE EXAMPLES FOR INTERMEDIATES

EXAMPLE A 2-(1-Methylethoxy)benzenamine

2-Nitrophenol sodium salt, 64.4 g (0.4 mol), and 67.99 9 (0.4 mol) of 2-iodopropane are combined in 400 ml N,N-dimethylformamide and stirred and refluxed overnight. The resulting mixture is cooled, concentrated in vacuo, and the residue taken up in water and the oil extracted into diethyl ether. The diethyl ether layer is separated, washed with 500 ml of 10% sodium hydroxide, water (2X), dried (magnesium sulfate), concentrated in vacuo to give after distillation 45.2 g (62.4%) of 1-(1-methylethoxy)-2-nitrobenzene, bp 99°-101° C. at 0.1 mm.

1-(1-methylethoxy)-2-nitrobenzene, 45.26 g (0.25 mol) is dissolved in 500 ml of methanol, 4 g Raney nickel is added and the mixture is exposed to hydrogen gas until the required amount of hydrogen is absorbed. The methanol solution is filtered and concentrated in vacuo and the residue distilled to give 35.7 g (94.4%) of 2-(1-methylethoxy)benzenamine; bp 100-102 (at 4 mm).

EXMAPLE B 2-(Hexyloxy)benzenamine

2-Nitrophenol, sodium salt, 48.33 g (0.3 mol), and 1-bromohexane, 49.5 g (0.3 mol) in 300 ml of N,N-dimethylformamide are stirred and refluxed overnight. The resulting mixture is cooled, filtered, concentrated in vacuo, water is added to the residue, and the oil is extracted into diethyl ether. The diethyl ether layer is separated, washed with 5% sodium hydroxide, brine (2X), dried (magnesium sulfate), concentrated in vacuo to give after distillation 61.9 g of 1-(hexyloxy)-2-nitrobenzene; bp 121°-124° C. at 0.075 mm.

1-(Hexyloxy)-2-nitrobenzene, 61.28 g (0.27 mol) is dissolved in 700 ml of methanol, 3 g Raney nickel is added and the mixture exposed to hydrogen gas until the required amount of hydrogen is absorbed. The methanol solution is filtered and concentrated in vacuo and the residue distilled to give 50 g of 2-(hexyloxy)benzenamine; bp 145°-148° C. at 4 mm.

EXAMPLE C

4-Methyl-2-(1-methylethoxy)benzenamine

A mixture of 23 g (150 mmol) of 5-methyl-2-nitrophenol 28.1 g (1.1 x 150 mmol) of 2-iodopropane and 22.8 g (1.1 x 150 mmol) of anhydrous potassium carbonate in 150 ml of acetonitrile is stirred and refluxed for 18 hours overnight. The solids were removed, the solvent evaporated and the residue is taken up in diethyl ether and the solution washed with 50 ml of 2N potassium hydroxide (2X), brine, dried (magnesium sulfate), and evaporated to an oil. Distillation gives 18.6 g (64%) of 5-methyl-1-(1-methylethoxy)-2-nitrobenzene; bp 98°-100° C. at 0.5 mm.

5-Methyl-1-(1-methylethoxy)-2-nitrobenzene, 17.7 g (91 mmol), is dissolved in methanol, palladium on charcoal is added and the mixture is exposed to hydrogen gas until the required amount of hydrogen is absorbed. The mixture is worked up in the usual manner to give 15 g of 4-methyl-2-(1-methylethoxy)benzenamine.

EXAMPLE D 5-(2-aminophenoxy)-2,2-dimethylpentanoic acid, methyl ester

A mixture of 27.8 g (200 mmol) of 2-nitrophenol, 44.6 g (200 mmol) of methyl-5-bromo-2,2-dimethylpentanoate (*Journal of Medicinal Chemistry, Vol.* 26, pp 1020–1027 (1983)) and 30.5 g (220 mmol) of anhydrous potassium carbonate in 300 ml of acetonitrile is stirred at reflux for 18 hours. The inorganic salts are removed, washed with acetonitrile and the filtrate is concentrated on a rotary evaporator. The residue is taken up in diethyl ether and the solution washed with 2N potassium hydroxide (3×50 ml), brine, dried (magnesium sulfate), and evaporated to afford 55.9 g of crude product. Distillation gives 52.9 g of 2,2-dimethyl-5-(3-nitrophenoxy)-pentanoic acid, methyl ester, bp 160°–165° C. (0.5 mm).

A solution of 5.6 g (20 mmol) of 2,2-dimethyl-5(3-nitrophenoxy)pentanoic acid, methyl ester, 0.5 g of 5% palladium on charcoal in 100 ml of methanol is shaken under three atmospheres of hydrogen gas until the hydrogen uptake is complete. The catalyst s removed and the solvent evaporated. The residual oil is taken up in toluene and evaporated to remove traces of methanol to afford 5-(2-aminophenoxy)-2,2-dimethylpentanoic acid, methyl ester.

EXAMPLE E 5-(3-Aminophenoxy)-2,2-dimethylpentanoic acid, methyl ester

In a process analogous to Example D by substituting 3-nitrophenol for 2-nitrophenol one obtains 5-(3-aminophenoxy)-2,2-dimethylpentanoic acid, methyl ester as an oil.

EXAMPLE F

5-[4-Amino-2,5-dimethylphenoxy)-2,2-dimethylpentanoic acid, methyl ester In a process analogous to Example D by substituting 2,5-dimethyl-4-nitrophenol for 2-nitrophenol one obtains 5-[4-amino-2,5-dimethylphenoxy)-2,2-dimethylpentanoic acid, methyl ester, monohydrochloride; mp 164°–166° C.

We claim:
1. A compound of Formula I

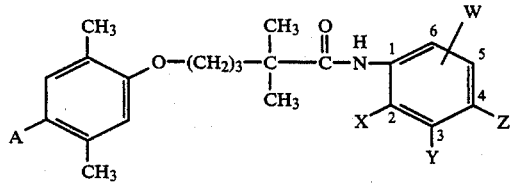

or a pharmaceutically acceptable acid addition salt thereof, wherein A is hydrogen, hydroxy, alkoxy of from one to six carbon atoms or

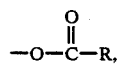

in which R is an alkyl group of from one to six-carbon atoms; X and Y are each independently hydrogen, fluorine, nitro, —NH$_2$, NHR, in which R is as defined above, —NRR, in which R is as defined above, alkyl of from one to six carbon atoms, or alkoxy from one to six carbon atoms which may be substituted at the terminal carbon atom by —CO$_2$R, in which R is as defined above; Z and W are each independently hydrogen, fluorine, alkyl of from one to six carbon atoms, or alkoxy of from one to six carbon atoms which may be substituted at the terminal carbon atom by —CO$_2$R, in which R is as defined above, and at least one of X, Y, Z or W is not hydrogen.

2. A compound as defined in claim 1 having the Formula II

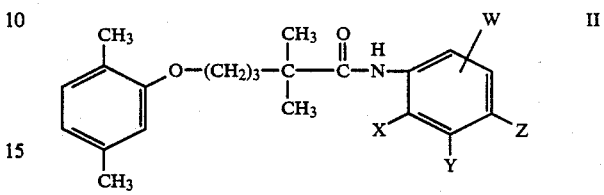

3. A compound as defined in claim 2 wherein X is hydrogen, fluorine, alkyl of from one to six carbon atoms, or alkoxy of from one to six carbon atoms which may be substituted at the terminal carbon atom by —CO$_2$R, in which R is as defined above; Y is hydrogen, nitro, —NH$_2$, —NHR, in which R is as defined above, —NRR, in which R is as defined above, alkyl of from one to six carbon atoms, or alkoxy of from one to six carbon atoms which may be substituted at the terminal carbon atom by —CO$_2$R, in which R is as defined above; Z is hydrogen, fluorine, alkyl of from one to six carbon atoms, or alkoxy of from one to six carbon atoms which may be substituted at the terminal carbon atom by —CO$_2$R, in which R is as defined above; and W is hydrogen, fluorine, alkyl of from one to six carbon atoms, or alkoxy of from one to six carbon atoms which may be substituted at the terminal carbon atom by —CO$_2$R, in which R is as defined above.

4. A compound as defined in claim 3 having the name -(2,5-dimethylphenoxy)-N-(2-methoxy-4-methyl-phenyl)-2,2-dimethylpentanamide.

5. A compound as defined in claim 3 having the name 5-(2,5-dimethylphenoxy)-N-(2,4-dimethylphenyl)2,2-dimethylpentanamide.

6. A compound as defined in claim 3 having the name 5-(2,5-dimethylphenoxy)-N-(2-ethoxyphenyl)2,2-dimethylpentanamide.2,2-dimethylpentanamide.

7. A compound as defined in claim 3 having the name N-(3,4-dimethoxyphenyl)-5-(2,5-dimethylphenoxy)2,2-dimethylpentanamide.

8. A compound as defined in claim 3 having the name 5-(2,5-dimethylphenoxy)-2,2-dimethyl-N[4-methyl-2-(1-methylethoxy)phenyl]pentanamide.

9. A compound as defined in claim 3 having the name N-(2,4-difluorophenyl)-5-(2,5-dimethylphenoxy)2,2-dimethylpentanamide.

10. A compound as defined in claim 3 having the name 5-(2,5-dimethylphenoxy)-2,2-dimethyl-N-(2,4,6trifluorophenyl)pentanamide.

11. A pharmaceutical composition useful for inhibiting the intestinal absorption of cholesterol and also for increasing high-density lipoprotein (HDL) cholesterol comprising an effective amount of a compound as defined by claim 1 in combination with a pharmaceutically acceptable carrier.

12. A method of inhibiting intestinal absorption of cholesterol and also increasing high-density lipoprotein (HDL) cholesterol in mammals comprising administering to said mammal an effective amount of a compound as defined by claim 1 in combination with a pharmaceutically acceptable carrier.

* * * * *

UNITED STATES PATENT AND TRADEMARK OFFICE
CERTIFICATE OF CORRECTION

PATENT NO. : 4,882,357
DATED : November 21, 1989
INVENTOR(S) : Paul L. Creger, et al.

It is certified that error appears in the above—identified patent and that said Letters Patent is hereby corrected as shown below:

In column 14, line 37, insert --5-- before -(2,5-

In column 14, line 44, delete --2,2-dimethylpentanamide.--

In column 14, line 55, insert -- - -- after 6

Signed and Sealed this

Twenty-third Day of October, 1990

Attest:

HARRY F. MANBECK, JR.

Attesting Officer

Commissioner of Patents and Trademarks